United States Patent
Murakami et al.

(10) Patent No.: US 9,023,017 B2
(45) Date of Patent: May 5, 2015

(54) OPHTHALMIC LASER TREATMENT APPARATUS

(75) Inventors: Naho Murakami, Toyokawa (JP); Koichi Ito, Toyohashi (JP)

(73) Assignee: Nidek Co., Ltd., Gamagori-shi (JP)

( * ) Notice: Subject to any disclaimer, the term of this patent is extended or adjusted under 35 U.S.C. 154(b) by 1911 days.

(21) Appl. No.: 12/076,496

(22) Filed: Mar. 19, 2008

(65) Prior Publication Data

US 2008/0243108 A1    Oct. 2, 2008

(30) Foreign Application Priority Data

Mar. 29, 2007  (JP) ................................ 2007-089636

(51) Int. Cl.
| | | |
|---|---|---|
| A61F 9/008 | (2006.01) | |
| G02B 27/09 | (2006.01) | |
| G02B 27/44 | (2006.01) | |
| A61B 18/20 | (2006.01) | |

(52) U.S. Cl.
CPC .......... *A61F 9/008* (2013.01); *A61B 2018/2035* (2013.01); *A61F 9/00821* (2013.01); *A61F 2009/00863* (2013.01)

(58) Field of Classification Search
CPC ..... A61F 9/008; G02B 27/044; G02F 1/3137; G11B 7/1356; G11B 7/1384; G11B 7/1395; G11B 7/1398
See application file for complete search history.

(56) References Cited

U.S. PATENT DOCUMENTS

| | | | |
|---|---|---|---|
| 7,044,943 B2 | 5/2006 | Murakami | |
| 7,082,151 B2 | 7/2006 | Momiuchi et al. | |
| 7,150,530 B2 | 12/2006 | Artsyukhovich et al. | |
| 2002/0151877 A1* | 10/2002 | Mason | 606/4 |
| 2005/0027288 A1 | 2/2005 | Oyagi et al. | |
| 2010/0174273 A1* | 7/2010 | Murakami | 606/4 |

FOREIGN PATENT DOCUMENTS

| | | |
|---|---|---|
| JP | A 2001-8945 | 1/2001 |
| JP | A 2003-310653 | 11/2003 |
| JP | A 2004-135971 | 5/2004 |
| JP | A 2004-229965 | 8/2004 |
| JP | A 2005-46247 | 2/2005 |
| WO | WO 00/73013 A1 | 12/2000 |

* cited by examiner

*Primary Examiner* — Lakshmi Channavajjala
(74) *Attorney, Agent, or Firm* — Oliff PLC

(57) ABSTRACT

An ophthalmic laser treatment apparatus comprises: a laser source that emits a laser beam for treatment of an affected part of a patient's eye; an optical fiber that transmits the laser beam emitted from the laser source; and a delivery optical system that irradiates the laser beam emitted from the optical fiber to the affected part of the patient's eye, the delivery optical system including: a plurality of diffraction optical elements each being configured to shape a beam profile of the laser beam at an emission end face of the optical fiber into a beam profile having one of a uniform intensity and a lower intensity in the center than on the periphery on the affected part and also to shape the laser beam to have a different spot size on the affected part of the patient's eye; and a changing unit which selectively disposing one of the diffraction optical elements on an optical path.

4 Claims, 4 Drawing Sheets

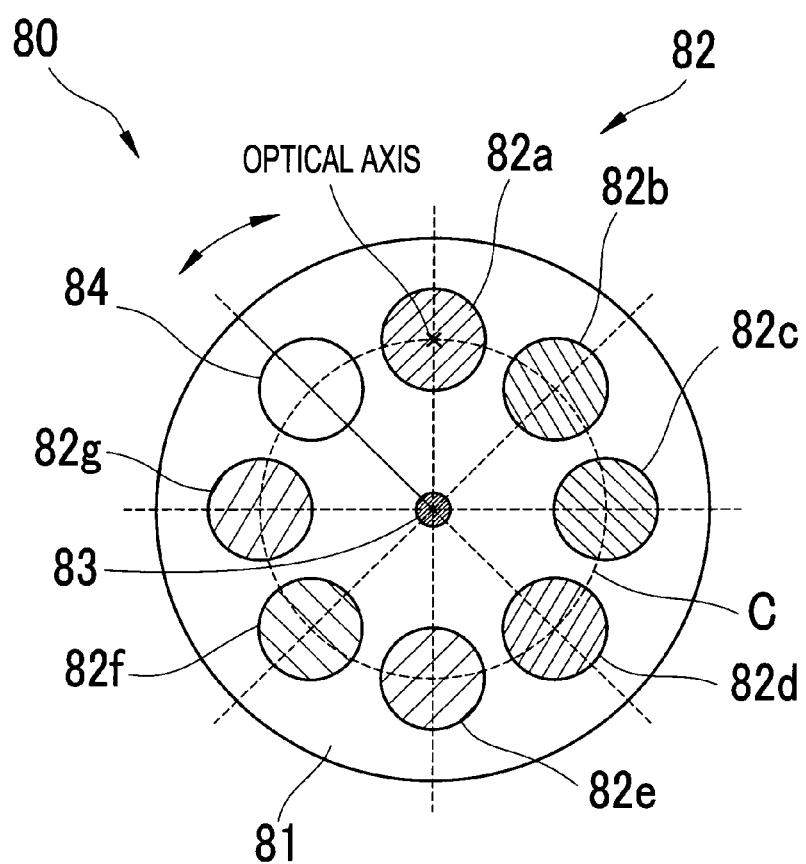

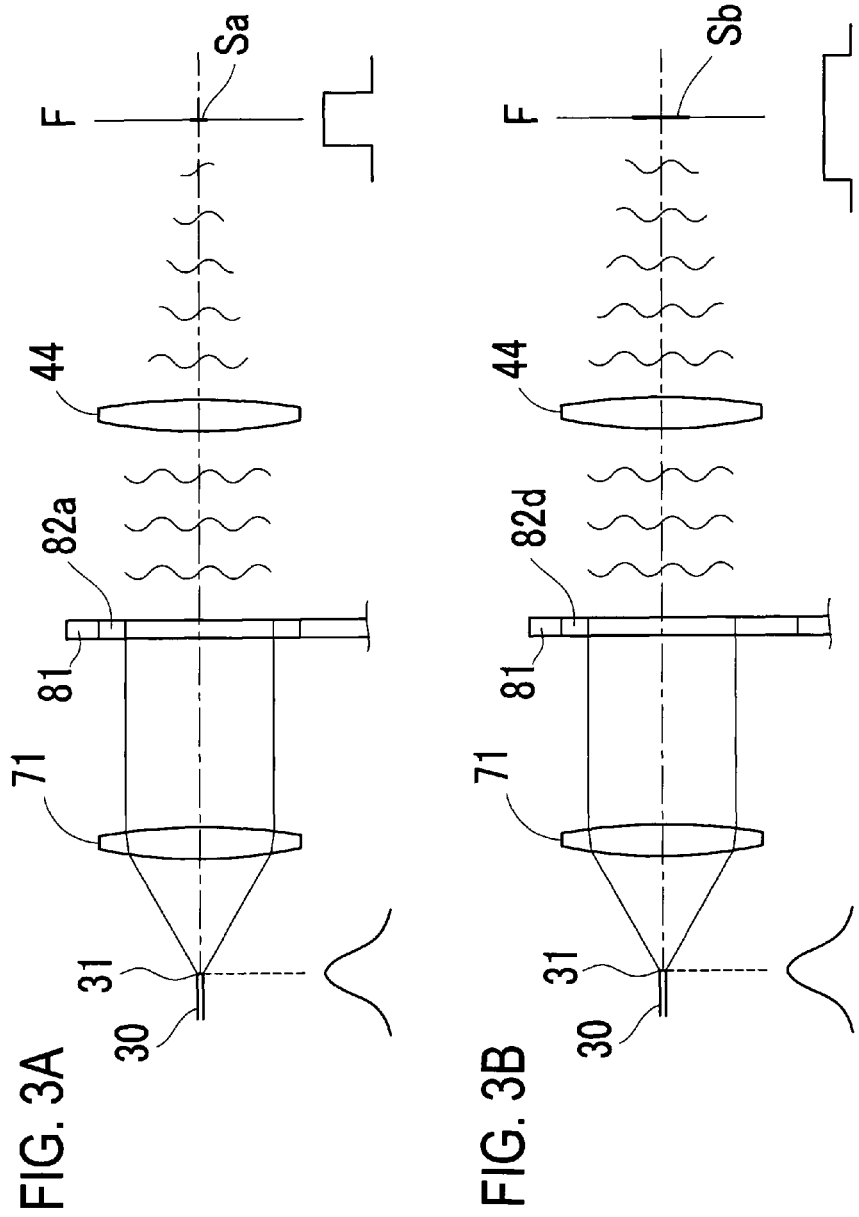

OPHTHALMIC LASER TREATMENT APPARATUS

BACKGROUND OF THE INVENTION

1. Field of the Invention

The present invention relates to an ophthalmic laser treatment apparatus arranged to irradiate a laser beam to a patient's eye for treatment.

2. Description of Related Art

An ophthalmic laser treatment apparatus arranged to irradiate a laser beam to a patient's eye includes a laser source which emits a treatment laser beam, an optical fiber for transmitting the laser beam from the laser source, and a delivery optical system provided with a variable power optical system for focusing the laser beam transmitted through the optical fiber at a spot size adequate for treatment purposes. An optical fiber used in a photocoagulation treatment laser apparatus is usually a multimode fiber having a core diameter of about 50 µm. Further, a delivery unit is provided with a variable zoom optical system for changing the laser spot irradiated on the fundus in a range of 50 µm to 500 µm. In laser iridotomy, the magnification of the variable zoom optical system is set at about 50 µm which is a minimum magnification so that energy density is increased in use.

Meanwhile, the multimode fiber is apt to generate a speckle pattern in a beam profile at a fiber emission end face. This may cause uneven burning in the fundus photocoagulation treatment, and hence a uniform coagulation spot could not be formed. In this regard, there have been proposed a technique of preventing the generation of a speckle pattern (refer to for example U.S. Pat. No. 7,082,151 (JP2004-135971A), US2005027288A1 (JP2005-46247), and JP2003-310653A) and a technique of changing an intensity distribution of a spot on an affected part (refer to for example JP2001-8945A, U.S. Pat. No. 7,044,943 (JP2004-229965A)).

The above proposed techniques have disadvantages such as a decrease in fiber transmittance, and a difficulty in placing and adjusting a mechanism for oscillating the multimode fiber. It is therefore desired to efficiently improve a beam quality by a simple structure. Further, in the case of using a single mode fiber instead of the multimode fiber, a beam profile at an emission end face of the single mode fiber is Gaussian, which would cause excessive coagulation in a center area of an irradiated part of an affected part. Furthermore, when a spot size of 50 µm to 500 µm is to be obtained on the fundus by use of a single mode fiber having a core diameter of about 5 µm, a variable power optical system capable of providing higher magnification is required. Such an optical system is difficult to manufacture. In the case where the aforementioned fiber is not used for transmission of a laser beam, for example, even in an apparatus including a laser source integral with a delivery optical system, a beam profile of the laser beam emitted from the laser source is Gaussian.

BRIEF SUMMARY OF THE INVENTION

The present invention has been made in view of the above circumstances and has an object to provide an ophthalmic laser treatment apparatus capable of irradiating a treatment laser beam having a beam characteristic adequate for treatment to an affected part and also of changing a spot size by a simple structure.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the above object, the present invention provides an ophthalmic laser treatment apparatus comprising: a laser source that emits a laser beam for treatment of an affected part of a patient's eye; an optical fiber that transmits the laser beam emitted from the laser source; and a delivery optical system that irradiates the laser beam emitted from the optical fiber to the affected part of the patient's eye, the delivery optical system including: a plurality of diffraction optical elements each being configured to shape a beam profile of the laser beam at an emission end face of the optical fiber into a beam profile having one of a uniform intensity and a lower intensity in the center than on the periphery on the affected part and also to shape the laser beam to have a different spot size on the affected part of the patient's eye; and a changing unit which selectively disposing one of the diffraction optical elements on an optical path.

Another object of the present invention is providing an ophthalmic laser treatment apparatus comprising: a laser source that emits a laser beam for treatment of an affected part of a patient's eye; and a delivery optical system that irradiates the laser beam emitted from the optical source to the affected part of the patient's eye, the delivery optical system including: a plurality of diffraction optical elements each being configured to shape a beam profile of the laser beam at an emission end face of the laser source into a beam profile having one of a uniform intensity and a lower intensity in the center than on the periphery on the affected part and also to shape the laser beam to have a different spot size on the affected part of the patient's eye; and a selectively changing unit which selectively disposing one of the diffraction optical elements on an optical path.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings,

FIG. 2 is a view of a variable power optical system viewed in an optical axis direction;

FIGS. 3A and 3B are diagrams to explain a mechanism of changing a spot size by DOEs.

DETAILED DESCRIPTION OF THE PREFERRED EMBODIMENTS

Figure 1:
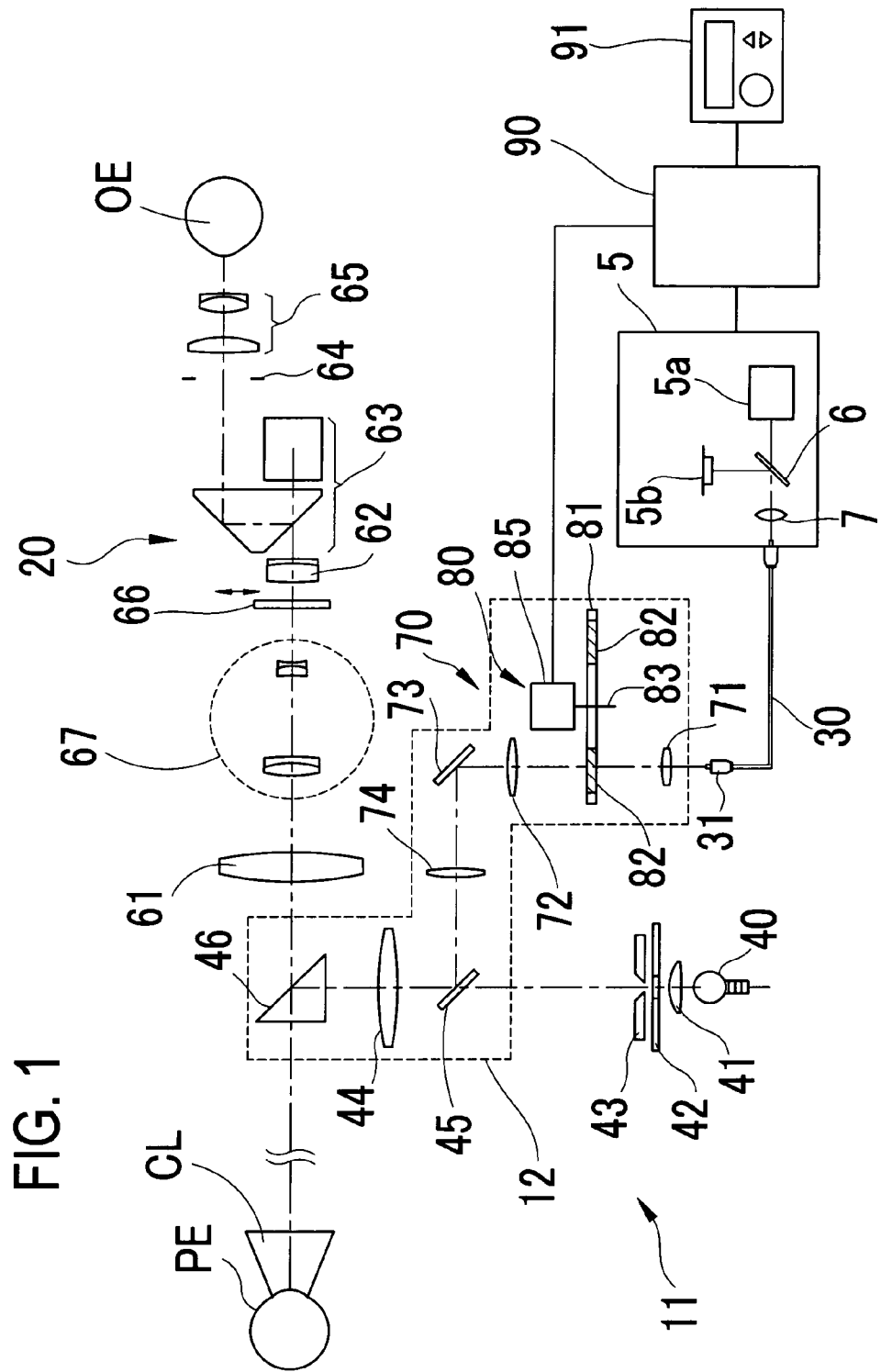
FIG. 1 is a schematic side view of an ophthalmic laser treatment apparatus.

A detailed description of a preferred embodiment of the present invention will now be given referring to the accompanying drawings. FIG. 1 is a schematic side view of an ophthalmic laser treatment apparatus of the present embodiment. In this embodiment, an apparatus for photocoagulating an affected part such as a fundus of a patient's eye is exemplified.

The laser apparatus includes: a slit lamp constituted by an observation unit 20 having a binocular microscope and an illumination section 11; a main box 5 in which a laser source is located; an optical fiber 30 for transmitting a laser beam from the main box 5; and a laser delivery optical system 12 for irradiating the laser beam emerging from the optical fiber 30 to the affected part such as the fundus, and others.

An observation optical system placed in the observation unit 20 includes an objective lens 61 used in common between right and left observation optical paths, a variable power lens unit 67, an operator protecting filter 66, an image forming lens 62, an erect prism 63, a field diaphragm 64, and an eyepiece 65. The components 62 to 67 are placed in each of the right and left optical paths.

An illumination light source 40 is provided in the illumination section 11. Visible light emitted from the illumination light source 40 passes through a condenser lens 41 and then is formed into a slit light beam having a height restricted by a variable aperture 42 and a width restricted by a variable slit plate 43. Thereafter, the slit illumination light passing through the variable slit plate 43 passes through a projection lens 44 and is reflected by a prism mirror 46 to illuminate the patient's eye PE. For observation of the fundus, illumination and observation may be conducted through a contact lens CL.

The main box 5 is provided with a treatment laser source 5a, an aiming source 5b which emits an aiming beam, and an optical system for delivering those laser beams. The laser source 5a is configured to emit a laser beam in a visible region. The laser source 5a is internally constituted by an excitation light source, a laser medium which absorbs excitation light and amplifies a specific wavelength (a wavelength in an infrared region in the present embodiment), a pair of mirrors forming a resonator to emit a laser beam, and a wavelength conversion element which converts an infrared laser beam to a visible laser beam which is a second harmonic wave thereof (all of them are not shown). The laser medium used in the present embodiment is an Nd:YAG crystal. The wavelength of the infrared laser beam amplified by the laser medium and the mirror becomes 1064 nm. The infrared laser beam is converted in wavelength to a visible laser beam of 532 nm by the wavelength conversion element, so that the laser beam of 532 nm is emitted as a treatment beam from the laser source 5a.

The aiming source 5b is constituted by a laser diode (LD) and emits a red laser beam in the present embodiment. The dichroic mirror 6 allows the treatment laser beam of 532 nm to pass therethrough and reflects the red laser beam serving as the aiming beam. Thus, the treatment laser beam and the aiming beam are coaxially aligned. The thus coaxially aligned treatment laser beam and aiming beam are made incident into the optical fiber 30 by the lens 7.

Those laser source 5a and aiming source 5b are connected to a control unit 90 for controlling output power and period of duration of the laser beam and switching on/off the aiming beam. The control unit 90 includes a controller 91 provided thereon with various switches for setting parameters for surgery such as the output power (an energy amount) of the laser beam to be irradiated and irradiation time, a switch for adjusting an illumination light amount, a switch for changing a spot size of the laser beam, and other switches. Based on the surgery parameters set with the above switches, the control unit 90 controls emission conditions of the laser beam of the laser source 5a and others and the spot size and others.

The treatment laser beam and the aiming beam emitted from the main box 5 are transmitted to the laser delivery optical system 12 through the fiber 30. The fiber 30 used in the embodiment of FIG. 1 is a single mode fiber having a core diameter of about 5 μm. Alternatively, a multimode fiber (e.g., a core diameter of about 50 μm) may be used.

The laser delivery optical system 12 includes a collimator lens 71 for collimating the laser beam emitted from a fiber emission end 31 into a parallel beam having an expanded beam diameter of about 10 mm, a disk 81 provided thereon with a plurality of diffraction optical elements (DOEs) for changing a beam profile of the laser beam and a spot size on a target plane (the fundus of the patient's eye), a relay lens 72, a mirror 73, a relay lens 74, a dichroic mirror 45 placed on an illumination optical axis of the illumination section 11, the projection lens 44 and the prism mirror 46 which are used in common with the illumination section 11. The dichroic mirror 45 has a property of reflecting most part of light of 532 nm which is a wavelength of the treatment laser beam, partly reflecting the red aiming beam, and partly transmitting white light emitted from the illumination light source 40, that is, a property of synthesizing the treatment laser beam coaxially with the illumination light with minimum loss.

The collimator lens 71, the plurality of DOEs 82, and the projection lens 44 which are included in the laser delivery optical system 12 constitute the variable power optical system 70 for changing the spot size of the laser beam emitted from the emission end face of the optical fiber 30 and irradiated to the affected part (on the fundus). The collimator lens 71, DOEs 82, and projection lens 44 also constitute a beam-profile shaping optical system for shaping an uneven laser profile at the emission end face of the optical fiber 30 into a desired beam profile on the affected part (the fundus). A shaft 83 is fixed in the center of the disk 81 on which the DOEs 82 are arranged on a circle. The shaft 83 is connected to a stepping motor 85. The disk 81 can be rotated by the motor 85 through the shaft 83. The motor 85 causes the disk 81 to rotate in response to a command signal from the control unit 90 so that one of the DOEs 82a to 82g is selectively disposed on the optical axis. The change of spot size is performed by the controller 91 (the details thereof will be mentioned later).

The configuration of the variable power optical system 70 also used as the beam-profile shaping optical system is explained below referring to FIG. 2 and FIGS. 3A and 3B. FIG. 2 is a view of a selectively changing unit 80 provided in the variable power optical system 70, viewed in the optical axis direction. FIGS. 3A and 3B are schematic diagrams to explain a mechanism of changing the spot size of the laser beam by the variable power optical system 70.

In FIG. 2, seven DOEs 82 (82a to 82g) are arranged on a circle C about the center of the disk 81. An aperture 84 allowing the laser beam to directly pass through is also formed on the circle C. The DOEs 82a to 82g and the aperture 84 are circumferentially spaced at equal angular intervals on the circle C. Rotation of the shaft 83 causes one of the DOEs 82a to 82g and the aperture 84 to be selectively disposed on (moved on or out of) the optical axis. The DOEs 82a to 82g are optical elements each of which includes a transparent body made of e.g. glass, quartz, or resin, formed with a large number of fine grooves arranged in a predetermined pattern for causing diffraction. Each DOE is designed so that laser beams having passed through the fine grooves causing diffraction overlap one another to form a spot of a desired size on the target plane (on the affected part). Even in the case where the beam profile at the emission end 31 of the optical fiber 30 has speckle noise or in the case where the beam profile is Gaussian, the laser beams having passed through the large number of fine grooves overlap one another to form an image on the target plane. Accordingly, this overlapping makes it possible to uniformize the beam profile on the target plane. The DOE may be designed so that the beam profile on the target plane has a lower intensity in the center than on the periphery. It is therefore unnecessary to strictly align the optical axis of the DOE and the optical axis of the laser beam incident on the DOE.

In the present embodiment, the DOE 82a is a diffraction optical element for forming a spot size of 50 μm and other DOEs are also designed so that the DOE 82b provides a spot size of 100 μm; DOE 82c, 200 μm; DOE 82d, 300 μm, DOE 82e, 400 μm; DOE 82f, 500 μm; and DOE 82g, 750 μm, sequentially.

Here, each DOE 82a to 82g may be arranged on the disk 81 in such a way that separately produced DOEs are mounted in the disk 81. In the present embodiment, however, the disk 81 is made of the same material as those of the DOEs 82a to 82g and the DOEs 82a to 82g are integrally formed with the disk 81. This configuration can save an assembly work and simplify the structure. The spot of the laser beam in the present embodiment is circular but the predetermined pattern of the fine groove of each DOE may be any shape.

Each of the DOEs 82a to 82g is designed in consideration of the following. Specifically, each DOE is designed and produced to provide a laser beam having a predetermined spot size and a rectangular profile in transverse section when an image is formed on the fundus of the patient's eye PE by the laser beam that has been collimated into a parallel beam having an expanded beam diameter of about 10 mm by the collimator lens 71, has passed through optical elements placed behind the collimator lens 71, that is, the relay lenses 72 and 74 and the projection lens 44 in the present embodiment, and then has passed through the contact lens CL.

In the present embodiment, the beam profile of the laser beam is formed into a uniform rectangular shape by the DOE 82, but not limited thereto. The beam profile only has to have an energy distribution enabling uniform photocoagulation of the fundus which is the target plane and an energy density not causing damages of an eye anterior segment. For example, the beam profile may be a trapezoidal shape or a shape lower in intensity at the center than the periphery.

The following explanation will be given to the spot size on the target plane (the fundus F) referring to FIGS. 3A and 3B. In FIGS. 3A and 3B, the relay lenses 72 and 74, the mirrors 73 and 45, and the contact lens CL are not shown. FIG. 3A schematically shows a beam profile of a laser beam at each point (the fiber emission end 31 and the fundus F). FIG. 3A is a diagram showing the case where the DOE 82a (a spot size of 50 μm) is disposed on the optical axis. FIG. 3B is a diagram showing the case where the DOE 82d (a spot size of 300 μm) is disposed on the optical axis. The laser beam emitted from the fiber emission end 31 is about 5 μm in diameter and is diverged to about 10 mm in diameter by the collimator lens 71. The collimated laser beam passes through the DOE 82a or 82d arranged on the disk 81 and hence forms an image of a desired spot size Sa (50 μm) or Sb (300 μm) on the fundus F. In FIGS. 3A and 3B, respective diffraction patterns of the DOEs 82a and 82d are produced in consideration of refractive power of the projection lens 44. The laser beam having passed through the DOE 82a or 82d is subjected to a diffraction effect and therefore cannot be illustrated by geometric light tracing. Thus, the laser beam is schematically illustrated by a wavy line as in FIGS. 3A and 3B.

In both cases shown in FIGS. 3A and 3B, the beam diameter on the disk 81 is about 10 mm. The spot sizes Sa and Sb depend on the DOEs 82a and 82d respectively.

At this time, the Gaussian beam profile at the emission end 31 or the beam profile with speckle noise is shaped into a rectangular form on the fundus F by the DOE 82 which is a beam shaping element. Accordingly, the energy distribution on the fundus F can be uniform, enabling photocoagulation treatment with reduced uneven burning. In the case where the beam diameter on the eye anterior segment is increased, the energy density on the eye anterior segment is decreased, thus reducing thermal damage or the like on the eye anterior segment in the photocoagulation treatment.

Further, one of the DOEs 82a to 82g is selectively disposed on the optical axis to obtain a laser beam of a desired spot size. Accordingly, as compared with the case of using the zoom optical system, the laser beam can be irradiated to the affected part without increasing an influence of aberration of each DOE.

As compared with the case of using the zoom optical system, a simpler structure can be achieved.

In the present embodiment, meanwhile, the beam diameter of the laser beam having passed through each DOE 82a to 82e is about 10 mm on the projection lens 44 for the following reasons. The beam diameter on the DOE 82a to 82g is about 10 mm (mentioned above). In the case of using the single mode fiber, a diffraction angle of the DOE 82 is as small as about 1 degree in the present invention. Accordingly, even in consideration of a distance between the DOE 82 and the projection lens 44 (generally, several tens millimeters), the beam diameter on the projection lens 44 is about 10 mm.

In the present embodiment, the variable power optical system 70 shares the projection lens 44 with the illumination section 11. The pattern of grooves (regions) of each DOE 82a to 82g is therefore designed taking into consideration the refractive power of the projection lens 44. However, the projection lens may be removed and a pattern for obtaining a laser beam of a desired spot size may be utilized.

Operations of the ophthalmic laser treatment apparatus having the above structure will be explained below. When the photocoagulation treatment is to be conducted on the fundus, an operator operates the controller 91 to determine various parameters (energy amount and irradiation time of a laser beam, etc.). The operator further selects a spot size. In response to a signal representing the selected spot size, the control unit 90 drives the motor 85 to rotate the disk 81 to dispose one of the DOE 82a to 82g corresponding to the selection signal on the optical axis. The operator holds the contact lens CL on the anterior segment of the patient's eye PE to restrict movement of the patient's eye PE. Then, the operator makes alignment of a laser irradiation point by use of a joystick (not shown) while the operator (an operator's eye OE) observes the affected part. The operator then depresses a footswitch (not shown) to irradiate the laser beam to the affected part of the fundus.

Treatment using laser iridotomy is explained below. In this treatment, the aperture 84 is selected and disposed on the optical axis. The laser beam emitted from the optical fiber 30 is irradiated to an iris which is a target plane after passing through the collimator lens 71, (the aperture 84), the relay lens 72, the mirror 73, the relay lens 74, the dichroic mirror 45, the projection lens 44, and the prism mirror 46. In the present embodiment, a focal distance of each of the collimator lens 71 and the projection lens 44 is determined so that the laser beam is irradiated to the iris at the same magnification (the same size) as that of the laser beam emitted from the emission end face 31. The fiber 30 is a single mode fiber whose core diameter is about 5 μm and hence the spot size on the iris is about 5 μm. In this way, the spot size is as small as about 5 μm, the energy density in the position of the spot is sufficiently high for iridotomy. Further, the laser beam irradiated to the iris has a Gaussian profile which is preferred in the iridotomy. This configuration is thus preferable.

In the case of using the single mode fiber providing a spot size of about 5 μm, the laser source 5a with output power in the order of 200 mW to 300 mW enables the iridotomy at sufficient high energy density. In the photocoagulation treatment, similarly, the laser source 5a has only to provide output power of 200 mW to 300 mW. As the laser source 5a, for example, a fiber laser source may be used.

The core diameter of the fiber 30 is about 5 μm, but not limited thereto. Even when the core diameter is about 10 μm, sufficient energy density can be obtained on the target plane.

The spot size in the iridotomy is not limited to the same size as the core diameter (the emission end diameter) of the single mode fiber. Any spot size may be adopted if only sufficient energy density for the iridotomy is obtained. For instance, it may be arranged such that an afocal optical system is constituted by setting an optical element such as a concave lens and a convex lens in the aperture 84 to change a beam diameter and form an image of a spot size of in the order of 5 μm to 10 μm on the target plane through the projection lens 44.

Figure 4A:
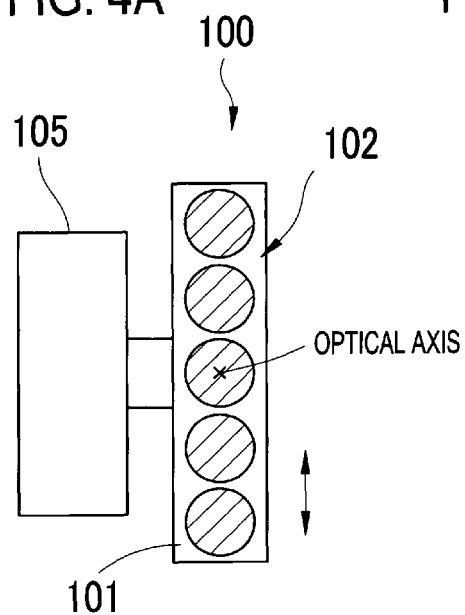
FIGS. 4A to 4D are diagrams to show modified examples of the invention.
Figure 4B:
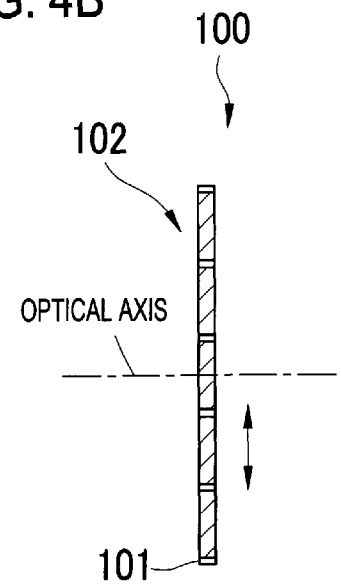
Figure 4C:
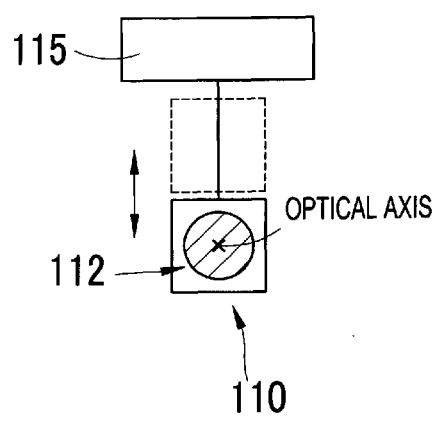
Figure 4D:
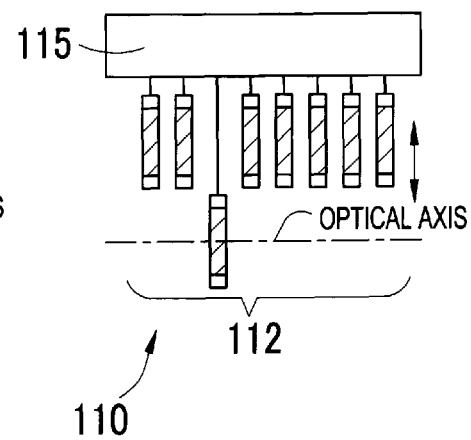

An explanation will be given to modified examples of the variable power optical system 70 of the present embodiment. FIGS. 4A to 4D are diagrams to explain a second embodiment and a third embodiment of the selectively changing unit provided in the variable power optical system. FIGS. 4A and 4B show the second embodiment. FIGS. 4C and 4D show the third embodiment. Specifically, FIG. 4A is a view of a selectively changing unit 100 seen in the optical axis direction. FIG. 4B is a sectional view seen from side. On a plate 101, DOEs 102 are different in diffraction pattern are arranged. The plate 101 is fixed to a slider 105 constituted by a linear motor or the like. In response to a command signal from the control unit 90, the slider 105 moves the plate 101 up and down as indicated by an arrow to dispose a desired DOE on the optical axis.

FIG. 4C is a view of a selectively changing unit 110 seen in the optical axis direction. FIG. 4D is a sectional view of the same seen from side. DOEs 112 different in diffraction pattern are individually connected to an actuator 115. In response to a command signal from the control unit 90, the actuator 115 moves each DOE 112 up and down as indicated by an arrow to move on or out of the optical axis. In the unit 110, the position of the DOE 112 disposed on the optical axis is different from DOE to DOE on the optical path. Accordingly, the diffraction pattern is determined in consideration of differences in distance from the selected DOE 112 to the projection lens 44. As described above, the diffraction angle of the laser beam by the DOE is small (here, about 1 degree), so that the beam diameter of the laser beam is not changed largely depending on the distance. Therefore, the DOE 112 may be designed without taking into consideration of the distance between each DOE 112 and the projection lens 44. That is, restrict alignment of each DOE in the axial direction is not required.

The treatment laser source 5a in the present embodiment may be configured by adopting a fiber laser that the laser diode (LD) is used as an excitation light source and the laser medium is used as an optical fiber. In the case of using the fiber laser, the infrared laser beam emitted from the fiber laser is converted to visible light by the wavelength converting element. At this time, the fiber of the fiber laser is preferably a single mode fiber.

In the present embodiment, it is arranged such that the DOEs 82a to 82g are moved on and out of the optical axis by the stepping motor 85 that is driven upon receipt of a signal from the control unit 90. In other words, the spot size is electrically changed. Alternatively, such change of spot size also may be manually operated. For instance, a rotary knob for changing spot size is provided in a slit lamp or another section so that the disk is rotated in association with the rotation of the rotary knob. The rotary knob is preferably configured to provide a sense of click to an operator to easily feel the change of spot size. The spot size changing and the beam shaping by the DOE need no strict alignment and hence may be conducted manually.

In the present embodiment, the optical fiber 30 is used as a medium for transmitting the laser beam emitted from the laser source 5a to the delivery optical system 12, but it is not limited thereto. Further, even where the beam profile at the emission end of the laser light source 5a is not Gaussian but includes speckle noise, the beam shaping on the affected part can be achieved by use of the DOE.

In a configuration that mirrors are arranged in the treatment laser source 5a to form a resonator, the mirror may be regarded as an output end. In another configuration that the treatment laser source 5a is a fiber laser or the like, an output end is a fiber emission end.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. An ophthalmic laser treatment apparatus comprising:
   a laser source that emits a laser beam for treatment of an affected part of a patient's eye;
   an optical fiber that transmits the laser beam emitted from the laser source; and
   a delivery optical system that irradiates the laser beam emitted from the optical fiber to the affected part of the patient's eye, the delivery optical system including:
   a plurality of diffraction optical elements, each being configured to shape the laser beam emitted from the optical fiber into a single spot having a beam profile having a different spot size from each other on the affected part of the patient's eye and also to shape the laser beam emitted from the optical fiber into a beam profile having either one of a uniform intensity and a lower intensity in a center than on a periphery on the affected part of the patient's eye; and
   a changing unit which selectively disposes one of the plurality of diffraction optical elements on an optical path, the changing unit being configured to change the diffraction optical elements on the optical path to change the spot size of the laser beam to be irradiated as a single spot on the affected part.

2. The ophthalmic laser treatment apparatus according to claim 1, wherein the optical fiber is a single mode fiber with that has a core diameter of about 5 μm and produces a Gaussian beam profile at an emission end face, and the diffraction optical elements include a plurality of diffraction optical elements each being configured to shape the laser beam to have a different spot size in a range of 50 μm to 500 μm on the affected part.

3. The ophthalmic laser treatment apparatus according to claim 1, wherein the changing unit is also arranged to dispose the diffraction optical element in a position out of the optical axis, and the delivery optical system includes a collimator lens that expands a diameter of the laser beam emitted from the optical fiber and collimates the laser beam, and a projection lens that projects the laser beam having passed through the diffraction optical element onto the affected part, and
   when the diffraction optical element is moved out of the optical axis, the emission end face of the optical fiber is projected by the collimator lens and the projection lens.

4. An ophthalmic laser treatment apparatus comprising:
   a laser source that emits a laser beam for treatment of an affected part of a patient's eye; and a delivery optical system that irradiates the laser beam emitted from the optical source to the affected part of the patient's eye, the delivery optical system including:
- a plurality of diffraction optical elements, each being configured to shape the laser beam emitted from the laser source into a single spot having a beam profile having a different spot size from each other on the affected part of the patient's eye and also to shape the laser beam emitted from the laser source into a beam profile having either one of a uniform intensity and a lower intensity in a center than on a periphery on the affected part of the patient's eye; and
- a changing unit which selectively disposes one of the plurality of diffraction optical elements on an optical path, the changing unit being configured to change the diffraction optical elements on the optical path to change the spot size of the laser beam to be irradiated as a single spot on the affected part.

* * * * *